US00PP22221P2

(12) United States Plant Patent
Iie

(10) Patent No.: US PP22,221 P2
(45) Date of Patent: Nov. 1, 2011

(54) ***HYDRANGEA* PLANT NAMED 'PERFECTION'**

(50) Latin Name: *Hydrangea macrophylla*
Varietal Denomination: Perfection

(76) Inventor: Ryoji Iie, Kyoto (JP)

( * ) Notice: Subject to any disclaimer, the term of this patent is extended or adjusted under 35 U.S.C. 154(b) by 0 days.

(21) Appl. No.: 12/799,524

(22) Filed: Apr. 27, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea macrophylla* named 'PERFECTION' that is characterized by its free-flowering and reblooming habit, and its well-developed mop-head type inflorescences comprised of double sterile flowers that are dark pink in color.

2 Drawing Sheets

Genus/species: *Hydrangea macrophylla.*
Varietal denomination: 'PERFECTION'.

CROSS REFERENCE TO A RELATED APPLICATION

This application is co-pending with U.S. Plant Patent Applications filed for a plant derived from similar parentage in the Inventor's breeding program that are entitled *Hydrangea* Plant Named 'PEACE' (U.S. Plant patent application No. 12/658,301)* and *Hydrangea* Plant Named 'FREEDOM' (U.S. Plant patent application 12/799,525)*.

BACKGROUND OF THE INVENTION

The present invention relates to a new and distinct cultivar of *Hydrangea macrophylla* and will be referred to hereafter by its cultivar name, 'PERFECTION'. 'PERFECTION' represents a new bigleaf hydrangea, a perennial shrub grown for landscape use.

'PERFECTION' was derived from an ongoing controlled breeding program by the Inventor that focuses on developing new cultivars of bigleaf hydrangeas with unique flower colors and double flowers. 'PERFECTION' originated from a cross conducted in the Inventor's trial garden in June 1996 in Kyoto, Japan between an unnamed plant of *Hydrangea macrophylla* from the Inventor's breeding collection as the female parent and *Hydrangea macrophylla* 'Yamaajisai' (not patented) as the male parent. The new *Hydrangea* was selected as a unique single plant from the progeny of the cross in 2000.

Asexual reproduction of the new cultivar was first accomplished by softwood stem cuttings in Kyoto, Japan in 2000 by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'PERFECTION' as a unique cultivar of *Hydrangea macrophylla.*

1. 'PERFECTION' exhibits double sterile flowers that are pink in color.
2. 'PERFECTION' exhibits a free flowering and repeating blooming habit; blooming from early May through early October in The Netherlands.
3. 'PERFECTION' exhibits well-developed mop-head type inflorescences.
4. 'PERFECTION' is sterile; fertile flowers do not open. 'PERFECTION' can be compared to its male parent, 'Yamaajisai', which differs from 'PERFECTION' in having smaller flowers, in having a flatter formed inflorescence, and in having weaker stems. 'PERFECTION' can be compared to its female parent, which differs from 'PERFECTION' in having fertile flowers that open and in having flowers that are lighter pink in color. 'PERFECTION' can be most closely compared to the cultivars 'FREEDOM', 'PEACE' and 'RIE 05' (U.S. Plant Pat. No. 18,508). 'Freedom' differs from 'PERFECTION' in having whitish to light pink flowers and 'PEACE' differs from 'PERFECTION' in having white flowers. 'PERFECTION' differs from 'RIE 05' in having longer internodes (6 cm versus 4 cm), bigger leaves, and wider inflorescences (20 cm versus 14 cm).

BRIEF DESCRIPTION OF THE DRAWINGS

The photographs in the figures were taken of a two year-old plant of 'PERFECTION' as grown under greenhouse conditions with ambient light in a 3-liter container in Leimuiden, The Netherlands.

The photograph in FIG. 1 illustrates a side view of 'PERFECTION' in full bloom.

Figure 1:
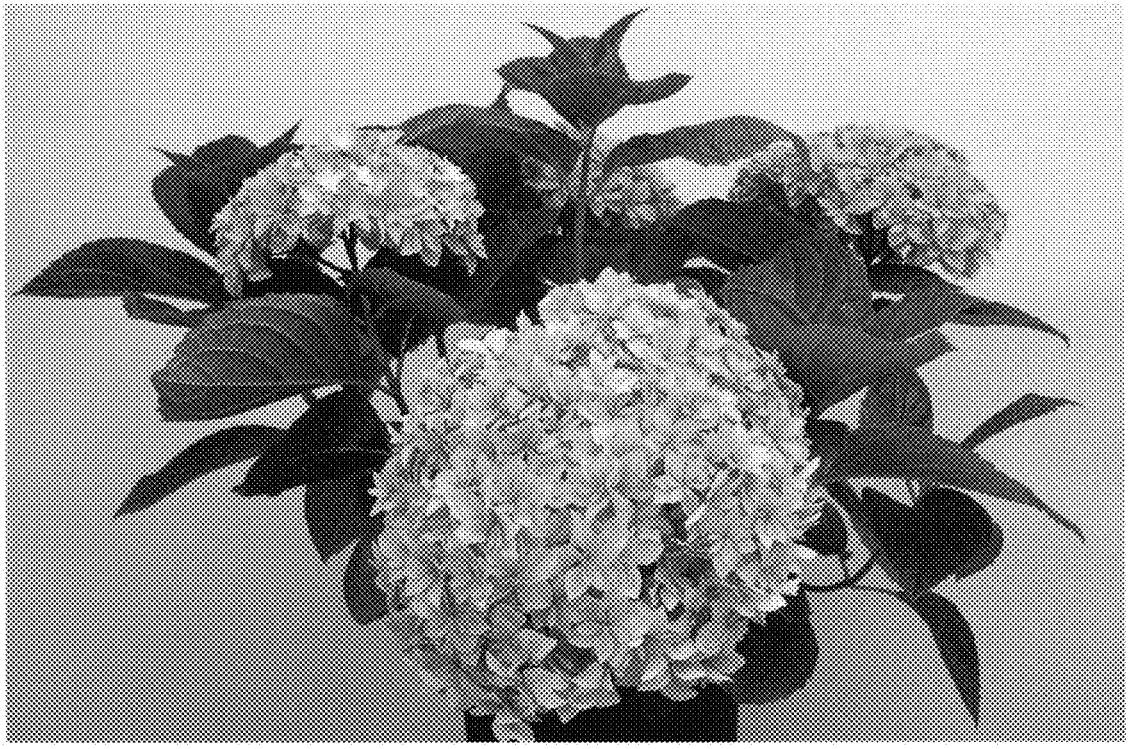
Figure 2:
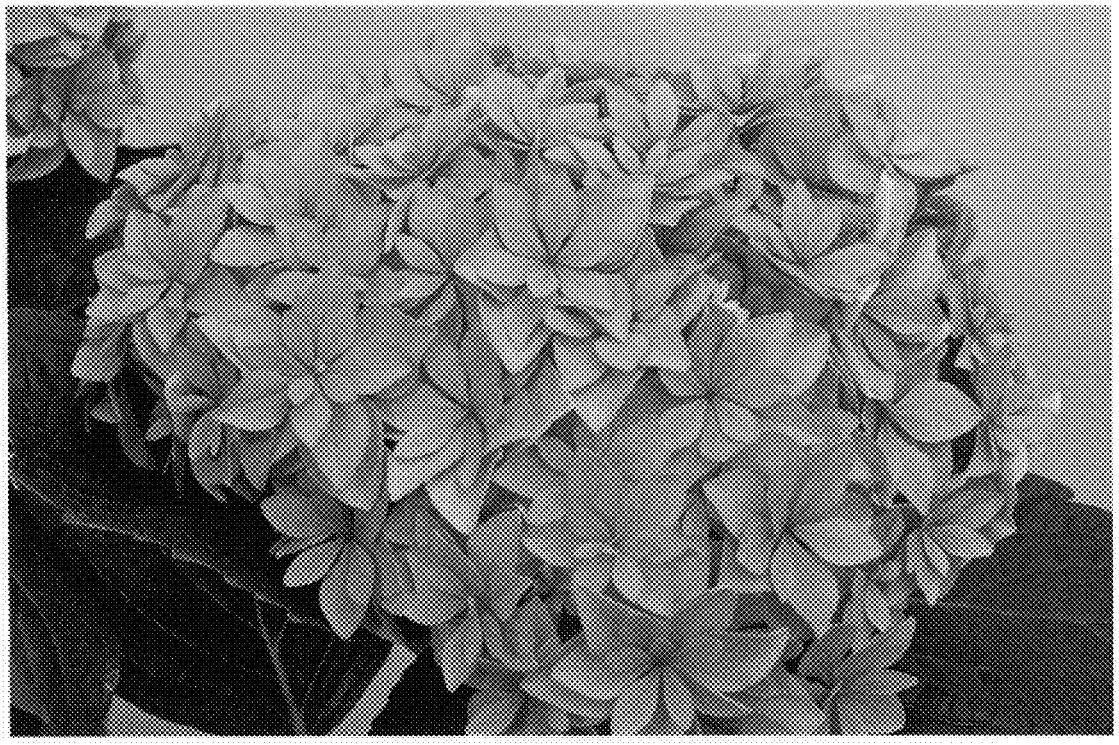

The photograph in FIG. 2 provides a close-up view of an inflorescence of 'PERFECTION'.

Figure 3:
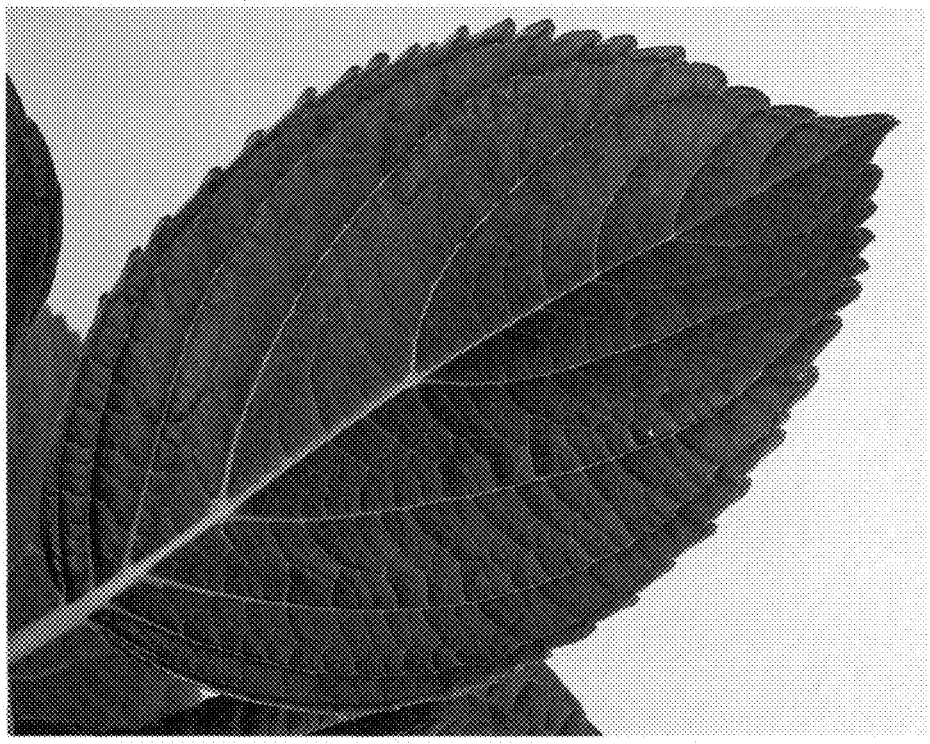

The photograph in FIG. 3 provides a close-up view of a leaf of 'PERFECTION'. The colors in the photographs are as close as possible with the digital photography and printing techniques utilized and the color codes in the detailed botanical description more accurately describe the new *Hydrangea.*

BOTANICAL DESCRIPTION OF THE PLANT

The following is a detailed description of two year-old plants of 'PERFECTION' as grown under greenhouse conditions in September with ambient light in 3-liter containers in Leimuiden, The Netherlands. The plants were grown under average day temperatures of 12° C. to 22° C. and average night temperatures of 8° C. to 18° C. Phenotypic differences may be observed with variations in environmental, climatic, and cultural conditions. The color determination is in accordance with The 2001 R.H.S. Colour Chart of The Royal Horticultural Society, London, England, except where general color terms of ordinary dictionary significance are used.

General description:

*Blooming period.*—Continuously from early May through October in The Netherlands.

*Plant habit.*—Broadly upright, deciduous shrub, sturdy, overall globular in shape.

*Height and spread.*—Average 39.1 cm in height and 69.7 cm in diameter.

*Hardiness.*—At least in U.S.D.A. Zones 5 to 9.

*Diseases resistance.*—Not more susceptible or resistant to pests and diseases than other *Hydrangea macrophylla* cultivars.

*Root description.*—Fibrous, dense.

Growth and propagation:

*Propagation.*—Softwood stem cuttings.

*Time required for root initiation.*—About 4 weeks during the summer and 5 weeks during the winter at an average temperature of 18° C. (night)/20° C. (day).

*Time required for root development.*—About 3 months to fully develop as a young plant when grown under greenhouse conditions at an average temperature of 18° C. (night)/20° C. (day) in summer or 8° C. (night)/12° C. (day) in winter.

*Time required to produce a salable crop.*—About 12 months from propagation to a flowering plant.

*Growth rate and vigor.*—Moderate, approximately 10 cm per month in spring.

Stem description:

*Stem shape.*—Round.

*Stem strength.*—Strong.

*Stem color.*—Immature stem; 144A to 144B in color, very sparsely covered with lenticels 1 mm in length and 0.5 mm in width, 1 per 3 sq cm, and 187A in color; mature stem; 199A to 199B.

*Stem size.*—Average of 26.5 cm (to base of inflorescence) and average of 5.5 mm in width.

*Stem surface.*—Glabrous, moderately glossy.

*Branching.*—Moderately branching, with an average of 9 lateral branches 26.5 cm in length and 5.5 mm in diameter.

*Internode length.*—Average of 6.1 cm, ranges from 3.5 to 9.7 cm.

Foliage description:

*Leaf shape.*—Broadly oval to broadly elliptic.

*Leaf arrangement.*—Opposite.

*Leaf division.*—Simple.

*Leaf number.*—Average of 8 (4 pairs) per lateral branch.

*Leaf base.*—Attenuate.

*Leaf apex.*—Acuminate.

*Leaf margins.*—Serrated.

*Leaf venation.*—Pinnate, upper and lower surface 145A to 145B in color.

*Leaf size.*—Average of 15.3 cm in length, ranging from 13.4 to 16.2 cm, and 11.3 cm in width, ranging from 9.6 to 12.8 cm.

*Leaf attachment.*—Petiolate.

*Leaf surface.*—Smooth, slightly glossy.

*Leaf color.*—Young foliage upper surface; a color between 141A and 143A, young foliage lower surface; 143A, mature foliage upper surface; a color between 137A and 147A, mature foliage lower surface; 138B.

*Petioles.*—Average of 3.1 cm in length, ranging from 2.5 to 5.0 cm, and 4.0 mm in width, 144B in color, surface is smooth and slightly glossy.

Inflorescence description:

*Inflorescence type.*—Terminal flattened-globular compound corymb of double rotate-shaped sterile flowers composed of an average of 15 sepals, fertile flowers form buds that do not open.

*Lastingness of inflorescence.*—Persistent with color lasting about 4 weeks.

*Inflorescence number.*—One per lateral or sublateral stem.

*Inflorescence size.*—Average of 12.0 cm in height and 20.8 cm in diameter.

*Flower number.*—An average of 180 sterile flowers per inflorescence, 10 fertile flowers per inflorescence.

*Flower fragrance.*—None.

*Flower aspect.*—Upright and outward.

*Flower size.*—Sterile flowers average of 4.3 cm in diameter, ranging from 3.9 to 5.4 cm, and 1.9 cm in depth, fertile flowers do not open, remain as buds.

*Flower buds.*—Fertile flowers; an average of 2.5 mm in length and 2 mm in width, obovate in shape, 144A to 144B in color.

*Peduncles.*—Average of 6.9 cm in length, ranging 40° angle to vertical, strong, 60C in color, glabrous surface.

*Pedicels.*—An average of 35 mm in length (ranging from 21 to 51 mm in length) and 1 mm in width, held at an average angle of 45° to vertical, 64A in color, moderate strength, glabrous surface.

*Petals.*—Absent.

*Sepals.*—Average of 15, rotate in arrangement, glabrous and dull surface (both surfaces), rhomboidal to narrowly elliptic in shape, margin is entire, tip bluntly acute, base cuneate, an average of 2.0 cm in length (ranging from 1.1 to 3.1 cm in length) and 1.4 cm in width (ranging from 0.5 to 2.1 cm in length), color when opening; 63B on upper surface and 63C to 63D on lower surface, color when fully opened, upper and lower surface; 68B with veins 67B in color.

Reproductive organs:

*Androecium.*—Not developed, fertile flowers do not mature.

*Gynoecium.*—Not developed, fertile flowers do not mature.

*Fruit and seed.*—None formed.

It is claimed:

1. A new and distinct cultivar of *Hydrangea* plant named 'PERFECTION' substantially as herein illustrated and described.

* * * * *